United States Patent [19]

Joh

[11] 4,329,383

[45] May 11, 1982

[54] NON-THROMBOGENIC MATERIAL COMPRISING SUBSTRATE WHICH HAS BEEN REACTED WITH HEPARIN

[75] Inventor: Yasushi Joh, Yokohama, Japan

[73] Assignee: Nippon Zeon Co., Ltd., Tokyo, Japan

[21] Appl. No.: 170,656

[22] Filed: Jul. 21, 1980

Related U.S. Application Data

[62] Division of Ser. No. 60,054, Jul. 24, 1979.

[51] Int. Cl.³ .................. A61F 1/00; B01D 39/18; D01D 5/24
[52] U.S. Cl. ................................... 428/36; 3/1; 8/120; 210/505; 210/500.2; 264/176 F; 264/209.1; 264/211; 424/183; 427/303; 427/324; 428/376; 428/398; 428/532; 536/66; 536/84
[58] Field of Search ............... 210/500 M, 505; 264/176 E, 177 F, 209, 211; 260/6; 424/183; 428/36, 376, 398, 532; 3/1; 427/303, 324; 8/120; 536/84, 66

[56] References Cited

U.S. PATENT DOCUMENTS

3,673,612  7/1972  Merrill et al. ............................... 3/1
3,810,781  5/1974  Eriksson et al. ...................... 424/183
4,127,625  11/1978  Arisaka et al. .................. 264/177 F

OTHER PUBLICATIONS

C.A. 85: 182374K.
Merrill et al., "Journal of Applied Physiology", 29(5), Nov. 1970, pp. 723–730.

Primary Examiner—James C. Cannon
Attorney, Agent, or Firm—Armstrong, Nikaido, Marmelstein & Kubovcik

[57] ABSTRACT

Non-thrombogenic material comprising a base polymer treated with heparin, the improvement in which the heparin is covalently bonded with the base polymer through only one acetal bond or hemiacetal bond at each bonding site between the heparin and the base polymer.

8 Claims, No Drawings

NON-THROMBOGENIC MATERIAL COMPRISING SUBSTRATE WHICH HAS BEEN REACTED WITH HEPARIN

This is a division of application Ser. No. 60,054, filed July 24, 1979.

BACKGROUND OF THE INVENTION

1. Field of the Invention

This invention relates to non-thrombogenic material, and particularly relates to polymeric material heparinized through covalent bonds. Said invention is particularly concerned with a novel procedure for producing said non-thrombogenic material.

2. Description of the Prior Art

In general, contact of blood with nearly any foreign surface leads to blood coagulation. This problem would severely limit the use of many otherwise useful medical procedures. The coagulation is initiated through an activation factor (also known as Hoegeman factor or Factor XII) that activates clotting factors culminating in polymerization of fibrinogen to fibrin. This surface-induced coagulation has presented obvious difficulties in such theraputic procedures as the use of an artifical kidney, heart, lung etc. Without systemic anticoagulants such as heparin, their use would have been impossible. Similarly, heart valves made from metals and polymeric materials produce emboli so that it is necessary to maintain patients on anti-coagulant therapy indefinitely.

In other procedures, for example, catheterization and blood shunting, a choice has had to be made between the systemic heparinization and the risk of clot formation. Systemic anti-coagulation is, of course, not a satisfactory answer due to control problems and the possibility of hemorrhage. In spite of all the foregoing difficulties, it is well known that artificial kidneys and blood oxygenators have been widely used. This is only made possible by administration of heparin, naturally occurring anticoagulant, into the patient's blood stream. Such procedures to prevent clotting are of a short-term nature, since the heparin is ultimately dissipated by the body. Thus, it has long been desirable that a material possessing long-term non-thrombogenic effect be materialized.

The first significant advance toward permanently non-thrombogenic surface has come with the development of heparinized surface by Gott et al. (Gott, V. L., Whiffen, J. D. and Dutton, R., Science 142, 1297 (1963)). In their procedure, graphite is first coated on the polymer surface. The graphite, in turn, serves to absorb a cation, usually benzalkonium group, which then ionically binds heparin molecule. The method of binding heparin to the surface of a polymeric material through a quaternized amine has been further developed by other researchers. In one instance, phenyl groups of polystyrene are chloro-methylated, quarternized with dimethylaniline and then subjected to binding with the heparin. In the above reaction, the heparin is bonded only ionically as a quarternary ammonium salt. The ionically bonded heparin does, in fact, slowly dissociate from the surface in the presence of blood. This means that anti-coagulant properties obtained with ionically-bonded heparin are of a short-term nature.

There have been several attempts with limited success to link or bind heparin covalently to a certain polymer. For example, polyvinyl alcohol is allowed to react with the heparin in the presence of a dialdehyde such as glutaraldehyde. This utilizes the reaction between the aldehydes and the hydroxyls on the adjacent carbon atoms to form 6-membered 1,3-dioxane ring. The procedure can link the heparin to the polymer with a covalent bond, from which permanent non-thrombogenic properties may be expected. The vital drawback of the above procedure lies in the fact that the bi-functional dialdehyde does not always react only between the heparin and the polyvinyl alcohol, but, more likely, reacts between the heparin molecules and also reacts between the polyvinyl alcohol molecules to form many heparin-heparin and polyvinyl alcohol-polyvinyl alcohol cross-linkages. This reaction procedure develops cross-linked heparin gels or the cross-linked polyvinyl alcohols. These products are, of course, unfavorable (undesired) by-products. The ideal picture of the reaction is that one aldehyde in the dialdehyde molecule reacts with the heparin while another aldehyde reacts with the polyvinyl alcohol so that the heparin and the polyvinyl alcohol are bonded each other through aldehyde-OH reaction. Also, as has been known, the anti-coagulant effect of the heparin is remarkably reduced by chemical modifications. Therefore, the linking of the heparin and the polyvinyl alcohol by the action of the dialdehyde can not be called "successful" in view of the fact that the non-thrombogenic property obtained is less than one would expect.

SUMMARY OF THE INVENTION

An object of this invention is to provide non-thrombogenic materials covalently linked with heparin without the formation of a by-product, and a method for producing such non-thrombogenic materials.

Another object of this invention is to provide a hollow fiber with long-term non-thrombogenic properties when exposed to blood, and a method for producing such hollow fiber.

A further object of this invention is to provide a method for producing non-thrombogenic materials which involves a reaction between heparin and aldehyde-containing polymers.

A still further object of this invention is to provide a method for producing non-thrombogenic materials between heparin and an aldehyde-containing polymer which is prepared by the cleavage of carbon-carbon bond by the reaction of periodic acid (or its salt) or lead tetraacetate to give aldehyde groups.

A still further object of this invention is to provide a medical device having non-thrombogenic properties.

A still further object of this invention is to provide a method for producing non-thrombogenic medical devices which are used in contact with blood, such as artificial kidney, heart, lung, devices in intravascular implantation or extra corporeal connections or prostheses, and membranes for blood dialysis, blood filtration and oxygenation.

According to an aspect of this invention, the invention is directed to non-thrombogenic material comprising a base polymer treated with heparin, in which the heparin is covalently bonded with the base polymer through only one acetal bond or hemiacetal bond at each bonding site between the heparin and the base polymer.

The above and other objects, features and advantages of this invention, will be apparent in the following description and examples.

DESCRIPTION OF THE PREFERRED EMBODIMENTS

This invention relates to a method for producing non-thrombogenic materials which involves a reaction between heparin and an aldehyde group-containing polymer. This invention differs from the prior art, which has been directed to linking heparin and a polymer by the function of a dialdehyde, in that the present invention does not involve undesirable side reactions such as heparin-heparin bonding or polymer-polymer bonding. Therefore, there are no unfavorable gelled materials formed as by-products and probably because of the minimum chemical modification of the heparin, non-thrombogenic properties of the composition of this invention are outstanding. This is surprising from the fact that it has been observed that the anti-coagulant function of heparin is appreciably decreased by any sort of chemical modification.

In practice of the present invention, the "aldehyde group-containing polymer" can be prepared by the polymerization or copolymerization of the monomer which has an aldehyde or aldehyde group-forming group, namely, acetal or hemiacetal group. Thus, the "aldehyde group containing polymer" means the polymer containing aldehyde group or aldehyde group-forming group such as acetal or hemiacetal along the polymer chain.

Examples of these monomers are acrolein, methacrolein, p-formyl styrene, N-formyl amino ethyl acrylamide, N-formyl ethyl acrylamide, formyl ethyl acrylamide, formyl ethyl methacrylate, ketene dimethyl acetal, ketene diethyl acetal, acrolein acetal, methacrolein acetal and so forth. The polymerization or copolymerization of this kind of the monomer with other copolymerizable vinyl compounds can be performed in the usual manner by using a common radical initiator. An example of the copolymerization is given below to form "aldehyde group-containing polymer". Allylidene diacetate ($CH_2=CH-CH(OAc)_2$) prepared by the reaction between acrolein and acetic anhydride can be copolymerized with another vinyl compound like vinyl acetate, which is subsequently hydrolyzed to an "aldehyde group-containing polymer" as follows:

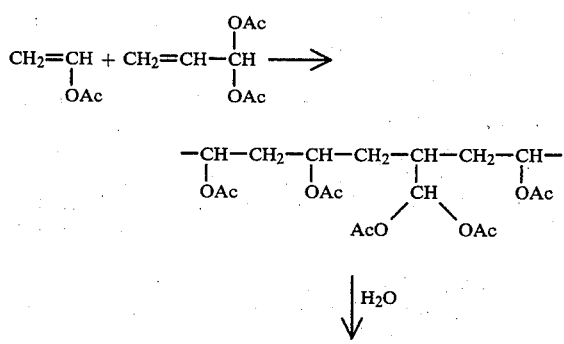

$$-CH-CH_2-CH-CH_2-CH-CH_2-CH-$$
$$\phantom{-C}|\phantom{H-CH_2-C}|\phantom{H-CH_2-C}|\phantom{H-CH_2-C}|$$
$$\phantom{-}OH\phantom{---}OH\phantom{---}CHO\phantom{--}OH$$

Other monomer such as vinyl chloride, acrylonitrile, methacrylonitrile, methyl methacrylate, isopropyl methacrylate, isopropenyl acetate, ethyl methacrylate, methyl acrylate, ethyl acrylate, methacrylic acid, acrylic acid, styrene, or α-methyl styrene may be used for copolymerization with "aldehyde group-containing monomer". The "aldehyde group-containing polymer" may be prepared, in turn, by periodic acid (or its salt) or lead tetraacetate cleavage of carbon-carbon bonds, which is a characteristic reaction of carbon-carbon bonds, where adjacent carbon atoms possess OH groups, i.e., vic-glycol. The typical polymers having vicinal hydroxyl groups can be natural polymers having glucose units. The natural polymers may be cellulose, cellulose derivatives such as oxycellulose, benzyl cellulose, cyanoethyl cellulose, cellulose acetate, polysaccharide, starch, gum arabic, chitin, chitosan, galactane, araban, galactomannane, xylane, alginic acid (or its salt), heparin and so forth.

These natural polymers have repeating glucose units in the chain molecule. The glucose unit has a vic-glycol moiety which can be cleaved by the action of periodic acid (or its salt), or lead tetraacetate as follows:

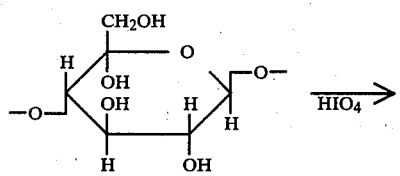

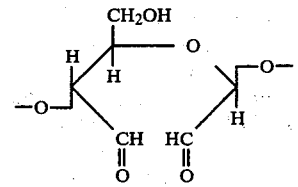

Therefore, by treating with periodic acid, the polymer having glucose units can be easily converted to "aldehyde group-containing polymer" ("P-CHO" will be used short for "aldehyde group-containing polymer".) by the simple treatment with periodic acid or lead tetraacetate. In the case of cellulose, the reaction can be visualized as follows:

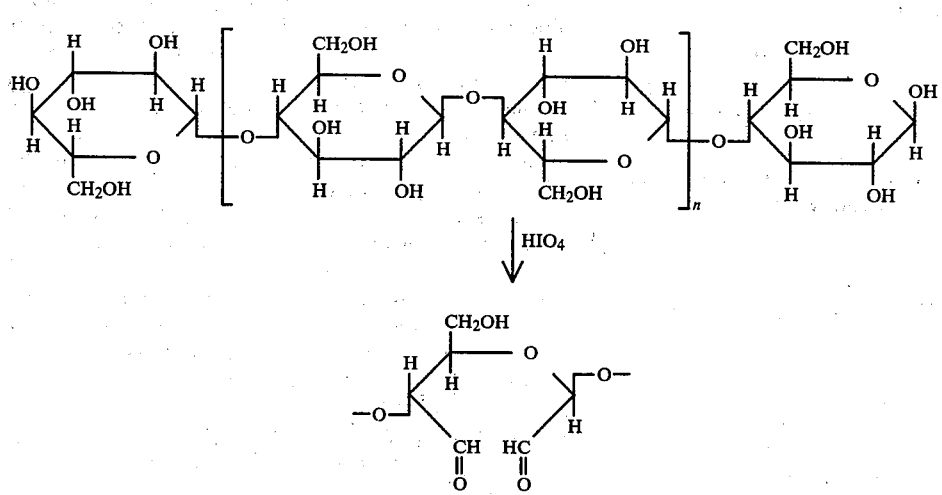

Hereafter, we use

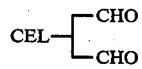

for the above reaction product

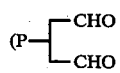

for generalization; P means polymer chain).

On the other hand, the chemical structure of heparin has a repeating unit described below:

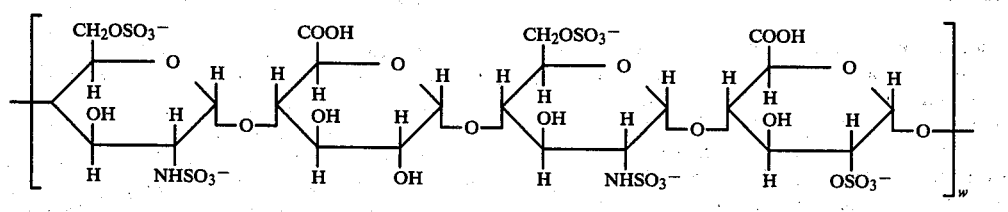

Heparin also has vic-glycol moieties in the chain. Hereafter we use simplified formula

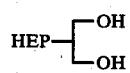

for heparin. The vic-glycol moiety in the heparin molecule reacts with an aldehyde in an acidic medium. Thus, the reaction between the vic-glycol moiety of the heparin and the aldehyde groups in the polymer forms a 5-membered ring, i.e., dioxolane ring which is very stable by nature, in accordance with the following reaction:

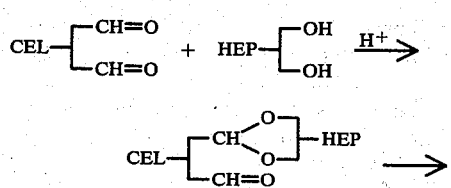

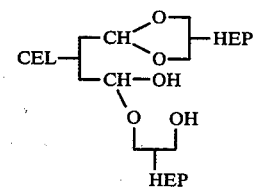

The hemiacetal structure is likely to be converted to more stable acetal by elimination of one water molecule.

The aldehyde group in the polymer may be converted to acetal or hemiacetal in the presence of an alcohol as follows:

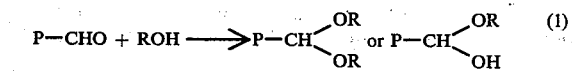

The chemical reactivity of acetal or hemiacetal shown above does not make any difference from "free" aldehyde, and these react with heparin in the same way as "free" aldehyde.

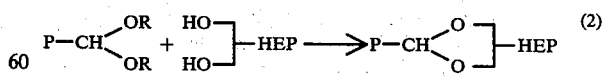

When the reaction (1) is carried out in an acidic medium in the presence of alcohol, hemiacetal structure may be formed.

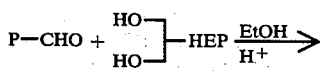

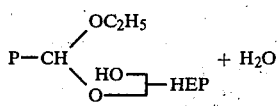

But this structure is liable to react further to form stabler 1,2-dioxolane ring by liberating ethanol.

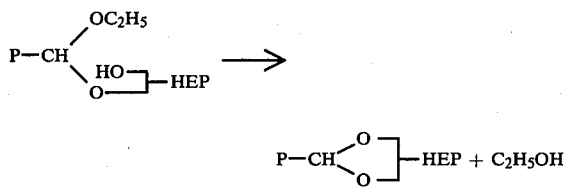

Thus, the reaction in this invention can be summarized as follows:

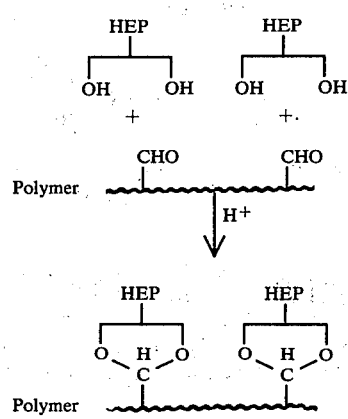

By the above reaction, heparin and the "aldehyde group-containing polymer" can be covalently bonded, which means that the linked heparin does not dissociate, thus, the heparin can not be leach out when exposed in the blood stream. In this reaction, there is neither a heparin-heparin side reaction, nor a polymer-polymer reaction as occurs to a great extent in the prior art.

In the present invention, from the principle of the above reaction, one can understand that any polymer which has aldehyde or acetal group can be obviously used. The polymer may be a homopolymer, copolymer, block copolymer or a graft copolymer and blends of the above polymers.

The aldehyde group-containing polymer contains preferably aldehyde group ranging from 1.0 to 20.0% by weight of the polymer, and heparin solution preferably has 50 to 100,000 USP unit heparin when applied to the reaction.

The above reaction can be carried out in a homogeneous phase or in a heterogeneous phase. For example, a water soluble starch is dissolved in water to form a homogeneous solution, treated with sodium metaperiodate and then allowed to react with heparin in an acidic medium. On the other hand, the surface of medical device which is exposed to blood can be coated with the above reaction product which can be rendered insoluble by the cross-linking with a dialdehyde such as glyoxal or glutaraldehyde. The invention may also be applied to any shaped article made from cellulose. For example, the interior of a cellulose hollow fiber, or cellulose tube may be treated with periodic acid to form aldehyde groups, followed by the above-described treatment with heparin. Cellulose film may also be treated in the same way.

The polymer treated is not always limited to a sole polymer, but may be a composite material or a blend material. This invention may be applied on the surface of a shaped article which is exposed to blood when in use. Thus, the coating material having aldehyde groups which can cover foreign surface may be utilized.

In the case of cellulose hollow fiber, the present invention may be applied in a hollow fiber manufacturing process. The inventor has already disclosed a novel method for producing cellulosic hollow fiber. According to his above-mentioned disclosure, cellulose ester, preferably cellulose acetate is dissolved in an organic solvent, for example, acetone. The hollow fiber can be spun through a "tube in orifice" spinnerete. The key to the success for forming the hollow fiber at a high speed (200 m/min) lies in the fact that a core solution which contains an effective amount of a salt which plays an important role in developing phase separation between the core solution and the spinning dope is used. Examples of said water soluble salt are sodium chloride, potassium chloride, calcium chloride, sodium phosphate, ammonium chloride, sodium acetate, sodium oxylate and so forth. When this technique is applied in the dry-jet wet spinning method, and spun-dope filament from the orifice is not gelled during the dry passage because the phase separation prevents the diffusing of the core solution into the sheath dope filament. Therefore, the spun dope-filament can be easily stretched during the air gap before being introduced into the coagulation bath.

The present invention may also be applied to the above hollow fiber producing process. When the core solution contains sodium metaperiodate, for example, in the form of a mixture with another water soluble salt such as sodium chloride, calcium chloride or sodium acetate, the inner surface or the hollow surface of the filament is contacted with sodium metaperiodate which selectively attacks vic-glycol of the cellulose ester to develop aldehyde groups. The core solution can contain an alkali metal hydroxide such as sodium hydroxide or potassium hydroxide. In this case, the inner surface or the hollow surface can be simultaneously hydrolyzed so as to regenerate cellulose, which is attacked simultaneously by the periodate to give rise to aldehyde groups. Preferable concentration of periodic acid or its salt in the core solution is 0.01 to 3 mol/l and more preferably 0.05 to 1.0 mole/l. When the concentration is lower than 0.01 mole/l, reaction will not proceed satisfactorily, and, when the concentration is more than 3.00 mole/l, degradation due to cleaverage of cellulose molecule may take place. The core solution may be acidic, for example, the core solution can contain periodic acid. This acidic core solution, can contain other inorganic or organic acids, such as hydrochloric acid, nitric acid, sulfuric acid or acetic acid. The solution also may contain neutral salts or acidic salts such as sodium chloride, potassium chloride, ammonium chloride, ammonium bromide and so on.

The hollow fiber thus formed can be successively treated with heparin in an acidic medium. Thus, heparin can be linked co-valently on the inner surface of the hollow fiber. The follow fiber thus obtained has a long-term, almost permanent non-thrombogenicity, which has long been needed.

The core solution may be an organic liquid containing periodic acid which does not gel the spinning solution, namely, a liquid having a swelling effect for the dope-polymer, or a solvent for the dope polymer. In this case, the core solution does not coagulate the spinning dope during the dry-passage (or in the air gap) when applied to dry-wet jet spinning method. The spun dope can be stretched before being introduced into the coagulation bath, where gellation take place instantaneously. This makes the spinning speed extremely high (180 m/min), compared to the known process. The example of this type of core solution may be formamide, dimethyl sulfoxide, dimethyl acetamide, dimethyl formamide, γ-butyrolactone, tetromethylene sulfone, 2-pyrrolidone, or mixtures of the above compounds, for cellulose acetate as dope polymer. These core solution can contain heparin to react based on the same principle.

The principle presented in the present invention can also be applied in a different mode. Heparin, which also contains vic-glycol, is first treated to form aldehyde groups in its molecule as follows:

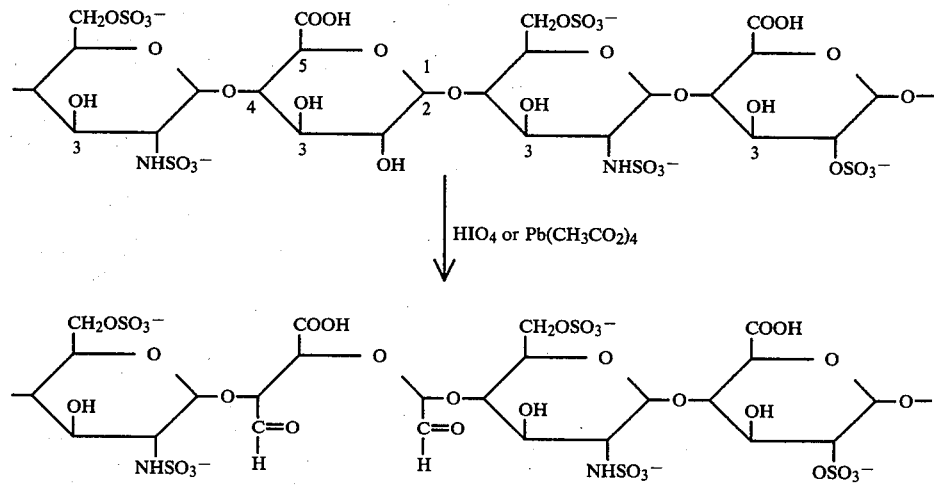

The product can react with a polymer having vicinal hydroxyl groups such as cellulose or polyvinyl alcohol as follows:

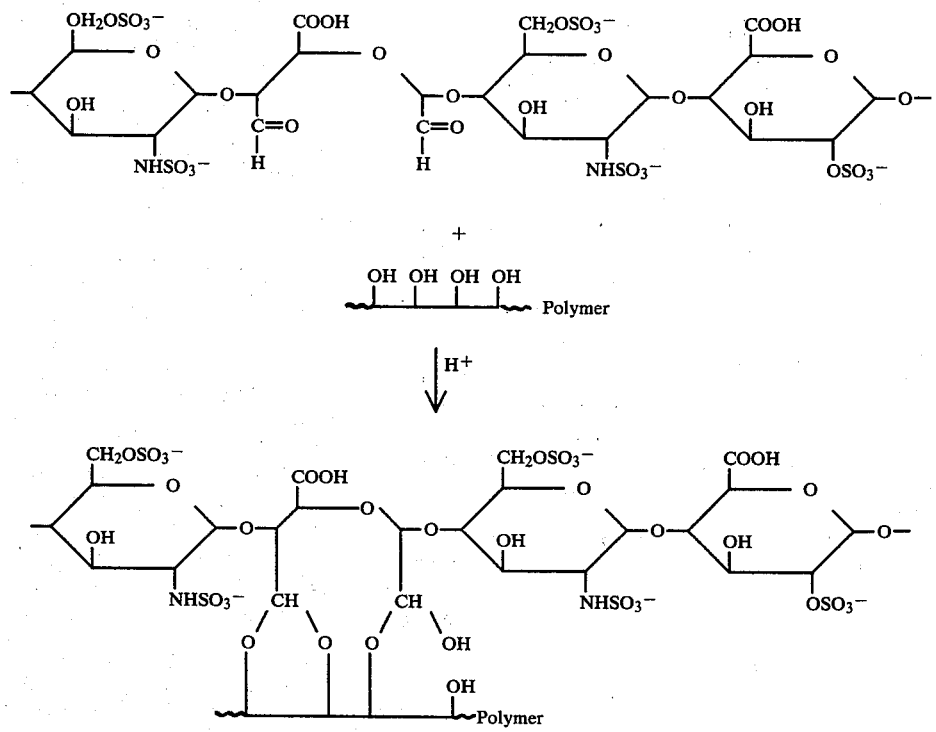

When the hydroxy polymer is cellulose, the heparin is linked through a 5-membered substituted dioxolane ring:

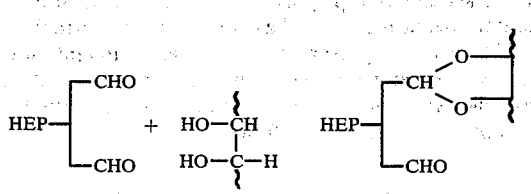

When the hydroxy polymer is polyvinyl alcohol, the acetal linkage is in the form of a 5-membered substituted 1,3-dioxane ring:

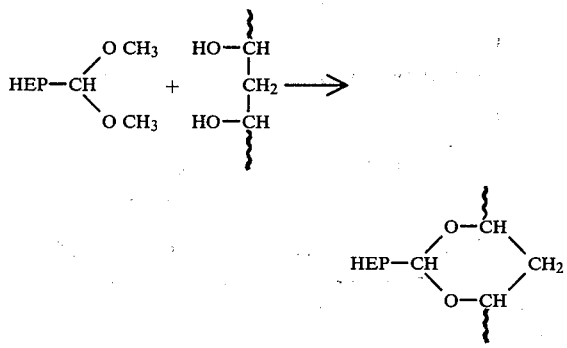

The both 5- and 6-membered acetal rings are very stable by nature, thus, the heparin molecules are bonded firmly by the covalent bonds. This is the reason why the above reaction products have long-term thrombogenicities.

The procedure presented in this invention can be applied in any form of the shaped articles. The invention also is applied as a coating material which has previously been subjected to this invention to link heparin. Also the present invention can be applied after being coated with the polymer having vic-glycol or aldehyde (or acetal) groups, through said functional groups. The heparin can be bonded as described in detail supra.

This invention is further illustrated in and by the following examples which are given merely as illustration and are not intended to restrict in any way the scope of the invention nor the manner in which it can be practiced.

EXAMPLE 1

Sodium metaperiodate was dissolved in 100 ml of water and the solution thus obtained was maintained at 5° C. Into this solution, a commercial cuprophane film prepared from cuproammonium solution was immersed for 30 minutes, the solution was then washed with distilled water and dried at ambient temperature. The film was next immersed in 50 ml of an aqueous solution containing 25,000 unit/ml heparin for 30 minutes at 40° C. The heparin solution was adjusted at pH 4 with sulfuric acid. After being treated in the heparin solution, the film was washed with water again, and dried at ambient temperature.

EXAMPLE 2

A 100 ml aqueous solution having 0.01 mole of sodium metaperiodate was adjusted to pH 8 with $H_2SO_4$. The solution was placed in a dark place at 10° C. Into this solution, a commercial cellophane film was immersed and allowed to react for 20 minutes. Then, the film was thoroughly washed with distilled water. The film was then allowed to react with heparin by being immersed in an aqueous solution having 5,000 unit/ml of heparin at pH of 3. Temperature was maintained at 50° C. during the reaction. After ten minutes, the film was taken up from the solution, washed with a sufficient amount of distilled water and then dried at ambient temperature.

EXAMPLE 3

50 g of water soluble starch was dissolved in 300 ml of water and the solution obtained was maintained at 30° C. To this solution, an aqueous solution (50 ml) containing 1 g of sodium metaperiodate was added, and the mixture was stirred for 10 minutes. The reaction product was precipitated by pouring the reaction mixture into large excess of methanol. The precipitant was filtered, and then the residual material was dissolved in water again. After the aqueous solution thus obtained had been adjusted to pH 3.5 with $H_2SO_4$, 5 ml of a solution having 25,000 unit/ml of heparin was added, and the solution was allowed to react at 40° C. for 30 minutes. The reaction mixture was again precipitated in a large excess of methanol under agitation. The precipitant was sufficiently washed with methanol. Purification of the reaction product was performed by re-precipitation using a water-methanol system. Thus, heparinized starch was obtained.

Using a tube made from polyvinyl chloride (100 mm long and 10 mm in inner diameter), a test tube was prepared by closing one end of the tube. The heparinized starch obtained above was dissolved in water to form a 25% solution; the pH thereof was adjusted to 1.0 with $H_2SO_4$ and an amount of glutaraldehyde calculated to form a 3% solution was added thereto. Immediately after the addition of the glutaraldehyde, the solution was poured into the polyvinyl chloride test tube, then the tube was rotated so that the inner surface was covered uniformly with the solution. After this operation, excess solution was decanted, then the tube was dried at 50° C. As the result, the inner surface was uniformly coated with cross-linked, heparinized starch.

Another experiment was conducted as follows, using soft-polyvinyl chloride film containing dioctyl phthalate (DOP) as a plasticizer: Immediately after the addition of glutaraldehyde to the acidic aqueous solution of the heparinized starch, the aqueous solution was coated on the surface of the film described in Example 2, then the coated film was heat-treated at 60° C. to evaporate water therefrom. As a result, glutaraldehyde-cross-linked heparinized starch, which is no longer soluble in water, was uniformly coated on the surface of the film. After being washed with a sufficient amount of water to eliminate the soluble portion, the film was dried at ambient temperature.

EXAMPLE 4

Using a tube made from cellulose butyrate acetate by Eastman Kodak Co., the following experiment was carried out. First, the inner surface of the tube was treated with 3 normal aqueous solution. By this procedure (KOH treatment), the inner surface of the tube was partially hydrolyzed to regenerate cellulose. After being washed thoroughly with water, the inner surface of the tube was contacted with the aqueous solution of sodium metaperiodate as in example 1 at 5° C. in dark place. After this, the periodate solution was removed from the tube, which was then washed with water. The water-washed tube was then immersed in an aqueous solution containing 10,000 unit/ml of heparin at pH 3 for 30 minutes at 40° C. The tube was then washed with water and dried.

EXAMPLE 5

Anti-coagulant tests were carried out using surface-heparinized film obtained in the examples 1 to 3. The following tests were employed. For comparison, unheparinized films of the same materials were tested as controls. The test for non-thrombogenetic properties was made by two methods described below:

The first method (Test I)

The film was first thoroughly washed with the saline solution, then placed on a watch glass. On this film, 1 ml of the fresh human blood was placed, then the test was made in such a manner that a silicon-coated needle was tipped into blood and pulled up, and checked if any fibrous material may be pulled up with the needle or not. The time that the fibrous material was first observed was defined as the initial coagulating time. The complete coagulation time was defined as the time that the blood was no longer flow down when the watch glass was tilted and tipped over.

The second method (Test II)

This test was carried out using dog's ACD blood. For one sample, 5 pieces of films were prepared and placed in watch glasses independently. These are kept at 37° C., then the fresh dog's ACD blood (0.25 ml each) was placed on every pieces of the films. Immediately after this, the addition of 0.025 ml of aqueous $CaCl_2$ solution, the concentration of which was 0.1 mole/l, was followed. This will start coagulation of the blood. After appropriate time intervals, coagulated blood mass was fixed with formation. This was again washed with water. After removing the water, the blood mass was weighed. The weight percent of the blood mass based on the control means which was prepared in the same condition on the glass plate.

The results obtained are summarized in the following table.

| Test Sample | | Test I Coagulation Time | | Test II |
|---|---|---|---|---|
| Kind | Heparinized | Initial | Complete | Blood Mass |
| Example 1 | yes | 300 min | >10 hrs | 3% |
| | no | 11 min | 16 min | 81% |
| Example 2 | yes | 240 min | >10 hrs | 6% |
| | no | 10 min | 19 min | 89% |
| Example 3 | yes | 240 min | >10 hrs | 8% |
| | no | 8 min | 14 min | 72% |
| Glass plate (control) | no | 6 min | 12 min | 100% |

From the above results, it is obvious that the heparinization in the present invention shows outstanding effect.

EXAMPLE 6

In this example, the tests of coagulation of the blood were examined using Lee-White method. Specimens used in this example were polyvinyl chloride tube coated with the heparinized starch obtained in the Example 3, and the partially hydrolyzed and heparinized cellulose acetate butyrate tube obtained in Example 4. For comparison, unheparinized tube specimens of the same kind, and glass test tubes with and without the treatment with silicone were tested in the same condition. The results are summarized in the following table.

| Tube Specimen | | Coagulation |
|---|---|---|
| Kind | Heparinized | Start Time |
| Example 3 | yes | >5 hrs |
| | no | 16 min |
| Example 4 | yes | >5 hrs |
| | no | 10 min |
| Glass tube* | — | 8 min |
| Glass tube** | — | 32 min |

*without treatment with silicone
**treated with silicone

REFERENCE EXAMPLE 1

215.2 mg of sodium heparin was dissolved in 100 ml of distilled water. To this, 0.0624 mole of sodium metaperiodate was added, and the mixture was kept for 28 hours at 5° C. By this procedure, one glycol per 16 glucose units of heparin was cleaved on an average. This solution was used as solution (I). After this solution was maintained for an additional 20 hrs in the dark, two glycols per 16 glucose units of heparin were cleaved. This solution was used as the solution (II).

EXAMPLE 7

The commercial Cuprophan ® and Cellophan ® film were cut to square (5×5 cm). The films were treated with solutions (I) and (II) at pH 3 adjusted with $H_2SO_4$ for 60 min. Temperature was maintained at 60° C. The films were then washed with water and dried.

EXAMPLE 8

A polyvinyl alcohol aqueous solution was prepared using a commercial polyvinyl alcohol. From the solution, a polyvinyl alcohol film was prepared by usual casting method. After heat-treatment of the film at 80° C. for 4 hours, the film became insolube in water because of the crystallization. This film was treated at pH 1.0 for 4 hours at 50° C. with solution (I).

EXAMPLE 9

A film made from a copolymer of vinyl acetate-ethylene copolymer was treated in a KCl saturated aqueous solution with 1 N of potassium hydroxide for 1 hour at 40° C. The surface of the film was hydrolyzed, which was confirmed by IR spectrum, showing the presence of —OH group. This surface-hydrolyzed film was treated with solution (II) at pH 1.0 for 1 hour at 40° C. The film was then washed with water and dried.

EXAMPLE 10

A commercial vinyl chloride-ethylene-vinyl acetate graft copolymer (GRAFTMER ® from the Nippon Zeon Co.) was shaped into a tube. The interior of the tube was hydrolyzed by contact with 2 normal potassium hydroxide aqueous solution. Thus interior surface of the tube became vinyl chloride-ethylene-vinyl alcohol copolymer. After being washed sufficiently, the tube was treated with solution (I) at pH 3 for 1 hour. Temperature was maintained at 30° C. After being washed with $H_2O$, the tube was cut to 10 cm length, and one end of the tube was heat-closed to form a test tube.

EXAMPLE 11

A tube from cellulose butyrate acetate was surface-hydrolyzed in the same manner as in Example 10. After being washed thoroughly with water, the tube was treated with solution (II) at 30° C. for 1 hour at pH 4.0.

EXAMPLE 12

Using the specimens obtained from Examples 7 to 11, non-thrombogenic properties were examined by the method proposed in Example 5. The results obtained are summarized in the following table.

| Test Specimen | | Test I Coagulation time | | Test II |
|---|---|---|---|---|
| kind | Heparinized | Initial | Complete | Blood Mass |
| Example 7 | yes | 230 min | >10 hrs | 3% |
|  | no | 8 min | 12 min | 82% |
| Example 8 | yes | 300 min | >10 hrs | 6% |
|  | no | 6 min | 17 min | 91% |
| Example 9 | yes | 120 min | >10 hrs | 8% |
|  | no | 5 min | 14 min | 88% |
| Glass | — | 8 min | 14 min | 100% |

From the above results, the effect of the present invention is obvious.

EXAMPLE 13

The tubes obtained by Examples 10 and 11 were tested by Lee-White method. For comparison, glass tubes were tested with and without silicone treatment. The results are summarized in the following table.

| Tube Specimen | | Coagulation |
|---|---|---|
| Kind | Heparinized | Start Time |
| Example 10 | yes | >10 hours |
|  | no | 13 min |
| Example 11 | yes | >10 hours |
|  | no | 18 min |
| Glass tube* | — | 12 min |
| Glass tube** | — | 43 min |

*without treatment with silicone
**treated with silicone

EXAMPLE 14

A film was prepared from the hydrolyzed product of the allylidene diacetate-vinyl acetate copolymer. The hydrolyzed product has acrolein unit (6.9 mole %) and vinyl alcohol unit in the polymer. By heat-treatment, the film became insoluble in water because of the crystallization. The film was immersed in the heparin solution containing 10,000 units of heparin for 30 min, which was adjusted at pH 3.0 with $H_2SO_4$. After being washed, the film was dried at ambient temperature.

EXAMPLE 15

A copolymer comprising methyl methacrylate and methacrolein (6.1 mole %) was dissolved in acetone. Using this solution, a film was casted by the usual method. The film was immersed in the solution containing 50,000 units of heparin for 40 minutes, adjusted at pH 2 with $H_2SO_4$. The dried film was presented for non-thrombogenetic test.

EXAMPLE 16

The powdered copolymer of methylmethacrylate and methacrolein was suspended in the aqueous solution containing 50,000 units of heparin at 50° C. for one hour at pH 3.2 adjusted with $H_2SO_4$. The polymer was filtered and dried. This was dissolved in acetone, and after the insoluble part had been removed, the solution was casted to form a film. The film obtained was presented for non-thrombogenicity test.

EXAMPLE 17

A copolymer of acrylonitrile-methyl acrylate-methacrolein acetal (86:9:5 by weight) was dissolved in dimethyl formamide. From the solution thus obtained, a film was prepared by casting the solution. The film was treated in boiled water to remove traces of dimethyl formamide retained in the film. This film was treated in the acidic aqueous solution having 10,000 units of heparin and the film was presented for non-thrombogenic test.

EXAMPLE 18

A copolymer of acrylonitrile-vinyl acetate-p-formyl styrene (91:3:6) was dissolved in dimethyl formamide. From this solution, a film was prepared in the same manner as in Example 17. Heparinization process was the same as in Example 17.

EXAMPLE 19

From homogeneous blend of 30 parts of methyl methacrylate-methacrolein copolymer (84:16) and 70 parts of soft-polyvinyl chloride plasticized with DOP (dioctyl phthalate) a tube having inner diameter of 8 mm was shaped. The tube was transparent and flexible. One end of the tube was heat-sealed to form a test tube. The test tube was filled with the heparin solution used in Example 17. After being stood over night at 30° C., the heparin solution was removed by decantation, and the tube was dried.

EXAMPLE 20

The non-thrombogenic tests were performed according to the method described in Example 5 using the film specimens obtained in Examples 14 to 18. The results are summarized in the below.

| Test Specimen | | Test I Coagulation Time | | Test II |
|---|---|---|---|---|
| Kind | Heparinized | Initial | Complete | Blood Mass |
| Example 14 | yes | 300 min | >10 hrs | 3% |
|  | no | 12 min | 16 min | 82% |
| Example 15 | yes | 260 min | >10 hrs | 2% |
|  | no | 8 min | 19 min | 89% |
| Example 16 | yes | 120 min | >10 hrs | 8% |
|  | no | 5 min | 14 min | 81% |
| Example 17 | yes | 280 min | >10 hrs | 4% |
|  | no | 6 min | 12 min | 86% |
| Example 18 | yes | 245 min | >10 hrs | 2% |
|  | no | 7 min | 12 min | 86% |
| Glass | — | 6 min | 12 min | 100% |

EXAMPLE 21

The non-thrombogenic test was performed by Lee-White Method using the tube obtained in Example 19. The result is shown with control data for comparison.

| Specimen | | Coagulation |
|---|---|---|
| Kind | Heparinized | Start Time |
| Example 19 | yes | >10 hrs |
|  | no | 14 min |
| Glass tube* | — | 8 min |
| Glass tube** | — | 32 min |

*without treatment with silicone
**treated with silicone

EXAMPLE 22

Cellulose acetate (Eastman Kodak Co., E-400-25) was dissolved in acetone-formamide mixture to form a spinning solution. The hollow fiber was produced using a "tube-in-orifice" spinneret, namely, the spinning solution was extruded through an annular slit, and simultaneously from a tube which was placed at the center of the annular orifice, core solution was introduced. The core solution (A) was a 20% aqueous solution of $CaCl_2$, while core solution (B) has 0.5 mole/l sodium metaperiodate in addition to 20% of $CaCl_2$. The spinning method employed was the so-called dry-jet wet spinning. The spun filament was introduced into a water coagulation bath after passing through an air gap of 30 cm. The filament was washed with water, and then wound up on a reel. This was immersed in water overnight, during that period, gradients in the core solution were dialyzed. In the inner surface of the hollow fiber prepared by using the core solution (B), the presence of aldehyde group was confirmed by infra-red spectrum. Interior surface of this hollow fiber was then treated with acidic (pH 2) heparin solution and then dried.

Hemodialyzers were assembled using the fibers obtained in this Example and, using each, blood dialysis was performed on a dog. There was observed non-thrombogenecity for the dialyzer assembled by use of the heparinized hollow fibers, while the hollow fiber without heparinization (using the core solution (A)) shows considerable blood clotting.

EXAMPLE 23

The same spinning solution in example 22 was used. Ammonium chloride was dissolved in 1 N HCl aqueous solution to form core solution (C). To this, 0.1 mole percent of periodic acid was added (core solution (D)). As in Example 22, the hollow fiber was prepared using the core solutions (C) and (D). The spinning was performed using usual dry-jet wet spinning (air gap:30 cm) as in example 22. The hollow fiber obtained on the reel was cut to be 30 cm long, then the core solution was removed from the hollow portion. The fiber was washed with water, followed by the treatment with acidic (pH 2) heparin solution. Using the hollow fibers thus obtained, a hemodialyzer was assembled. The non-thrombogenenic properties of the dialyzer were tested using a dog. The hollow fiber dialyzer using the heparinized hollow fibers obtained in this example shows no blood clotting.

EXAMPLE 24

Except for the use of the core solution having 0.1 mole of periodic salt (potassium periodate) in propylene glycol-water mixture (55:45), all the procedure was the same as in Example 22. The hollow fibers wound up on the reel was cut to be 30 cm long, then the core liquid was removed. The fiber was then treated with dilute acetic acid, then washed with $H_2O$, followed by the treatment with the heparin solution acidified with HCl. The hemodialyzer using this hollow fibers shows a minimum clotting of the blood, and outstanding effect of the present invention was confirmed.

What I claimed is:

1. A shaped article comprising a hollow fiber having an interior wall with a non-thrombogenic surface, said non-thrombogenic surface being prepared by reacting an aldehyde group or aldehyde groups or an aldehyde forming group or aldehyde forming groups on the interior wall with heparin.

2. The shaped article according to claim 1 wherein said heparin was contained in a core liquid which was extruded simultaneously with said dope to spin said hollow fiber.

3. The shaped article according to claim 1, wherein said hollow fiber was spun by extruding a dope of cellulose ester while simultaneously extruding an aqueous core liquid that contained a salt for developing a phase separation between said dope and said core liquid and a cleaving agent for cleaving carbon-carbon bonds between carbon atoms of said cellulose ester with vicinal hydroxyl groups, thereby developing said aldehyde groups.

4. The shaped article according to claim 3, wherein said core liquid further contained a hydrolyzing agent which hydrolyzed said cellulose ester at the interior wall of said hollow fiber to produce regenerated cellulose possessing vicinal hydroxyl groups which then reacted with said cleaving agent.

5. The shaped article according to claim 3 wherein said core liquid was an organic liquid containing periodic acid which did not gel said dope.

6. The shaped article according to claim 3 wherein said cleaving agent was periodic acid, a salt of periodic acid or lead tetraacetate.

7. A shaped article selected from the group consisting of a tube, a hollow fiber, a film and a sheet, coated with a non-thrombogenic material prepared by reacting cellulose ester with a cleaving agent to develop adjacent aldehyde groups on said cellulose ester and binding heparin to said adjacent aldehyde groups through acetal bond or hemiacetal bond at each bonding site between said heparin and said cellulose ester.

8. The shaped article according to claim 7 wherein the non-thrombogenic material was made insoluble by cross-linking with a dialdehyde.

* * * * *